US007094727B2

(12) United States Patent
Hwang et al.

(10) Patent No.: US 7,094,727 B2
(45) Date of Patent: Aug. 22, 2006

(54) HETEROPOLYACID CATALYST AND METHOD FOR PRODUCING THE SAME

(75) Inventors: Gyo-hyun Hwang, Daejeon (KR); Won-ho Lee, Daejeon (KR); Min-ho Kil, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/024,809

(22) Filed: Dec. 30, 2004

(65) Prior Publication Data

US 2005/0153831 A1   Jul. 14, 2005

(30) Foreign Application Priority Data

Jan. 9, 2004   (KR) .................... 10-2004-0001574

(51) Int. Cl.
*B01J 27/14*   (2006.01)
*B01J 27/24*   (2006.01)
*B01J 27/19*   (2006.01)
*B01J 27/185*  (2006.01)

(52) U.S. Cl. .................. 502/208; 502/200; 502/201; 502/209; 502/210; 502/211; 502/213

(58) Field of Classification Search ........ 502/208–211, 502/213, 200, 201
See application file for complete search history.

(56) References Cited

U.S. PATENT DOCUMENTS

| 4,301,031 | A  |   | 11/1981 | Shaw et al. |
|-----------|----|---|---------|-------------|
| 4,558,028 | A  |   | 12/1985 | Tsuneki et al. |
| 4,564,607 | A  | * | 1/1986  | Yoneda et al. .............. 502/209 |
| 4,621,155 | A  |   | 11/1986 | Ueshima et al. |
| 6,171,998 | B1 | * | 1/2001  | Lee et al. .................... 502/304 |
| 6,333,293 | B1 |   | 12/2001 | Kase et al. |
| 6,458,740 | B1 | * | 10/2002 | Kasuga et al. .............. 502/211 |
| 2001/0039240 | A1 | * | 11/2001 | Fukumoto et al. ............ 502/26 |
| 2002/0193246 | A1 | * | 12/2002 | Kasuga et al. .............. 502/208 |

FOREIGN PATENT DOCUMENTS

KR   1996-0003796   3/1996

* cited by examiner

*Primary Examiner*—J. A. Lorengo
*Assistant Examiner*—Patricia L. Hailey
(74) *Attorney, Agent, or Firm*—McKenna Long & Aldridge LLP

(57) ABSTRACT

Provided is a novel heteropolyacid catalyst useful for partial oxidation of methacrolein (MACR) to methacrylic acid (MAA), as represented by the following formula 1:

$$PMo_a A_b B_c C_d D_e E_f O_g \qquad (1)$$

wherein A, B, C, D, E, a, b, c, d, e, f, and g are as defined in the specification. Provided is also a method for producing the heteropolyacid catalyst. The heteropolyacid catalyst produced by the method exhibits excellent catalyst activity in terms of conversion rate, selectivity, and yield.

7 Claims, 3 Drawing Sheets

[Fig. 1]
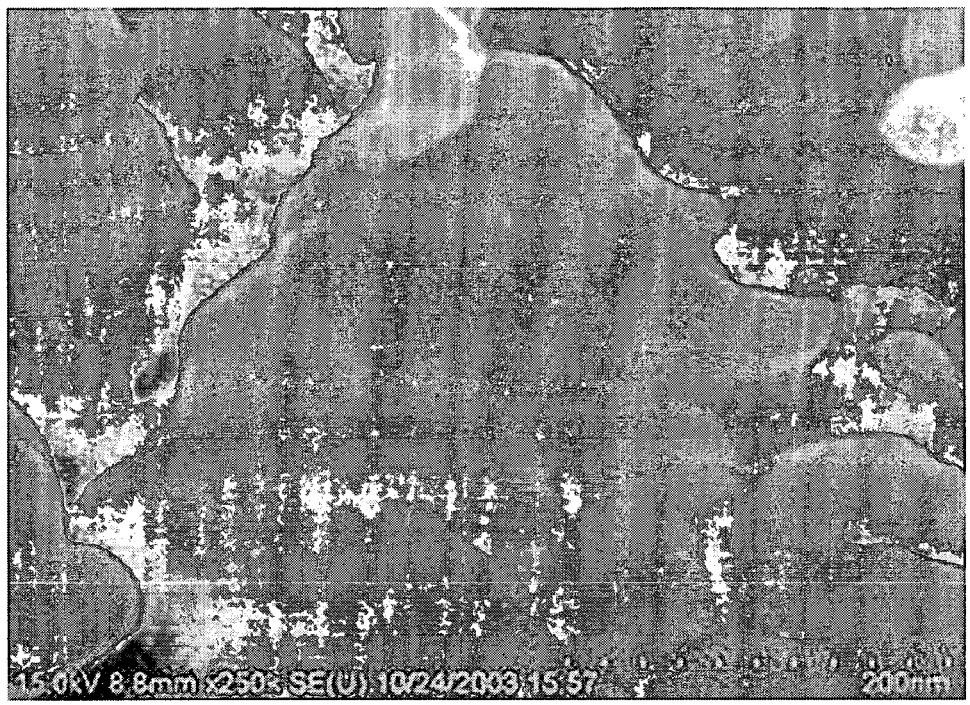
[Fig. 2]

[Fig. 3]
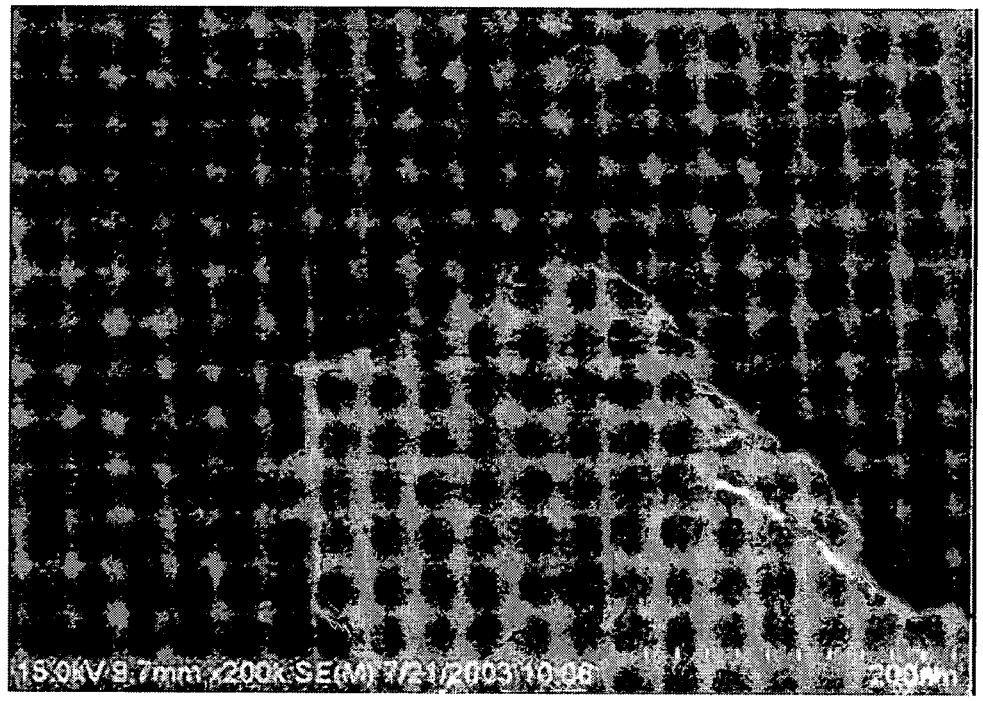
[Fig. 4]
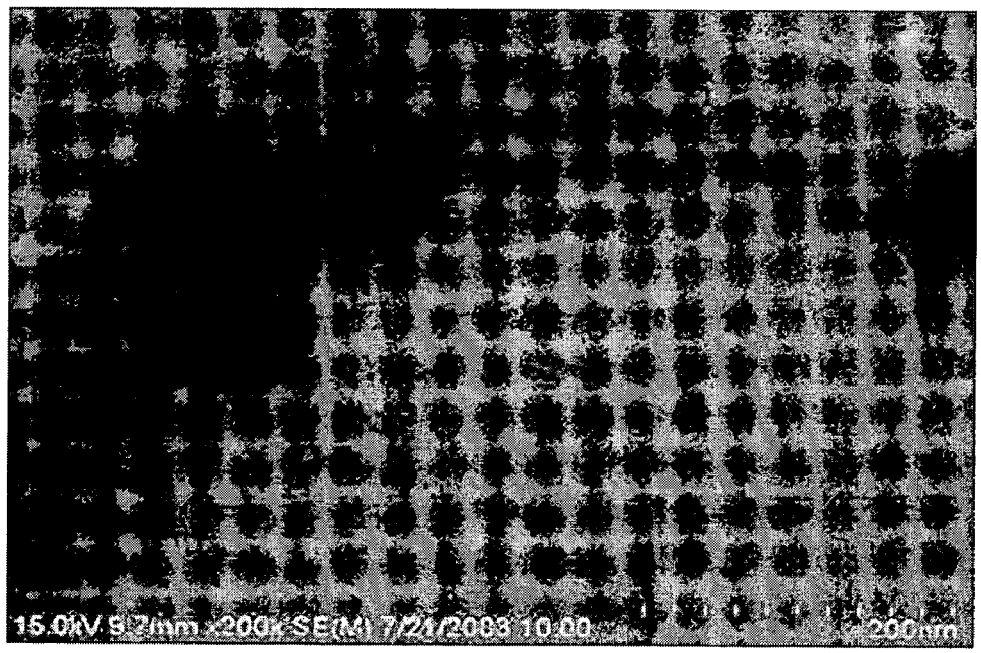

HETEROPOLYACID CATALYST AND METHOD FOR PRODUCING THE SAME

This application claims the benefit of the Korean Application No. 10-2004-000 1574, filed on Jan. 9, 2004, which is hereby incorporated by reference for all purposes as if fully set forth herein.

1. Technical Field

The present invention relates to a phosphomolybdate-based heteropolyacid catalyst which is useful in vapor-phase oxidation of methacrolein, as represented by the following formula 1:

$$PMo_aA_bB_cC_dD_eE_fO_g \quad (1)$$

wherein A, B, C, D, E, a, b, c, d, e, f, and g are as defined herein below. The present invention also relates to a method for producing the heteropolyacid catalyst.

2. Background Art

Japanese companies such as Nippon Shokubai Chemical Ltd. (NSCL) hold a majority of patents about a heteropolyacid catalyst for partial oxidation of methacrolein to methacrylic acid by a vapor-phase oxidation process. In these patents, a catalyst precursor is mainly prepared by coprecipitation with nitric acid or by vacuum drying in the absence of nitric acid.

Meanwhile, U.S. Pat. No. 4,301,031 describes that a heteropolyacid catalyst with a composition of $Mo_{12}P_{0.1-3}M_{0.1-3}Cu_{0.1-2}V_{0.1-2}X_{0.01-2}Y_aO_b$ (M is K, Rb, or Cs; X is Ba, La, Ga, Al, Ag, Cd, Ti, Tl, Hg, Pb, or Zn; Y is Fe, Co, Ni, Sr, Mn, In, Ta, Ge, S, or Be) is useful for the oxidation of methacrolein. The heteropolyacid catalyst with the above-described composition is produced to a final catalyst by drying, forming into a predetermined shape, and calcination. During the forming into a predetermined shape, pellets with a diameter of 5 mm and a length of 5 mm are generally formed. Decomposable ammonium or nitrate species are decomposed by the heat treatment to complete a catalyst with a desired structure and composition. The calcination is performed at a temperature of 300–500° C. under an oxygen or nitrogen atmosphere.

U.S. Pat. No. 4,621,155 describes that the preparation of a heteropolyacid catalyst in the presence of an N-containing material such as pyridine, piperidine, and piperazine can enhance formability and physical strength of the catalyst and reproducibility of the catalyst preparation.

A heteropolyacid catalyst production method varies according to the type of a metal-containing catalyst precursor. However, ammonium paramolybdate and ammonium metavanadate are mainly used.

According to a catalyst production method disclosed in Example 1 of U.S. Pat. No. 6,333,293B1, ammonium paramolybdate and ammonium metavanadate are dissolved in heated water with stirring and an appropriate amount of 85% phosphoric acid is added thereto. Then, cesium nitrate and copper nitrate are added to the resultant solution followed by heating and drying to produce a catalyst.

A catalyst production method disclosed in Example 12 of U.S. Pat. No. 4,558,028 follows the same manner as in Example 1 of U.S. Pat. No. 6,333,293B1 except that an appropriate amount of 85% phosphoric acid is added together with an appropriate amount of pyridine, and nitric acid is added before the addition of cesium nitrate and copper nitrate.

U.S. Pat. No. 6,458,740B2 discloses a method for producing a heteropolyacid catalyst including adding pyridine and 85% phosphoric acid to a solution containing ammonium paramolybdate and ammonium metavanadate, adding nitric acid, cesium nitrate, and copper nitrate to the resultant solution to induce coprecipitation, followed by heating and drying. This patent describes that activity and selectivity of a catalyst are affected by the ratio of $NH_4/Mo_{12}$ and $NH_4/NO_3$ contained in catalyst precursors.

Meanwhile, Korean Patent No. 1996-0003796 describes that transition metal ions such as Cu ion can be efficiently precipitated using a mixture of pyridine with oxalic acid.

In spite of these many inventions, since common heteropolyacid catalysts have low activity, there is an increased need to improve the conversion rate of methacrolein or selectivity to methacrylic acid. Furthermore, there is a problem in that productivity is lowered due to the low yield of a catalyst.

In addition, formation of a Keggin structure is prerequisite for production of a heteropolyacid catalyst. Reaction of a molybdenum precursor, a vanadium precursor, and a phosphoric acid partially forms a precipitate but these components are partially present in their dissolved forms in water. At this time, when the pH of the solution is lowered using nitric acid or the like, crystals are created and precipitated. When nitric acid is dropwise added in the absence of a transition metal, an ammonium ion-containing heteropolyacid is formed. At this time, nitric acid can be precipitated together with another transition metal, which is called coprecipitation. Therefore, a Keggin anion structure is created and bonds with another transition metal as a cation to form a precipitate.

Generally, it is known that coprecipitation leads to uniform precipitation of a transition metal. However, in a heteropolyacid production process, precipitation by nitric acid and transition metal salt formation are simultaneously performed, and thus, there is a high likelihood of non-uniform precipitation.

Some transition metals may not form water-insoluble salts of them with heteropolyacid at low pH. Copper is the most representative metal. In this respect, as described above, even though coprecipitation is used for preparation of a heteropolyacid catalyst, copper ions remain in their dissolved forms without being precipitated and makes a blue color solution.

To solve these problems, a prepared catalyst slurry is dried in vacuum or heated above the boiling point of water so that metal ions are uniformly distributed in a catalyst simultaneously with drying of the slurry.

DISCLOSURE OF INVENTION

While searching for solutions to these problems, the present inventors found a method for producing a heteropolyacid catalyst by preparing an ammonium ion-containing heteropolyacid using nitric acid followed by addition of a metal precursor, unlike a conventional catalyst production method by coaddition and coprecipitation of a transition metal and nitric acid. At this time, when a transition metal carbonate, instead of a common transition metal nitrate, is used as the metal precursor, dispersion of a metal component is enhanced, thereby increasing catalyst activity. The present inventors thus completed the present invention.

Therefore, the present invention provides a novel heteropolyacid catalyst represented by formula 1.

The present invention also provides a method for efficiently producing the heteropolyacid catalyst of the formula 1.

The above and other objects of the present invention can be accomplished by embodiments of the present invention as will be described hereinafter.

According to an aspect of the present invention, there is provided a heteropolyacid catalyst represented by the following formula 1:

$$PMo_aA_bB_cC_dD_eE_fO_g \quad (1)$$

wherein A is V, Nb, or W; B is an alkali metal or an alkaline earth metal; C is Cu, Ag, Co, Ni, Pb, Mn, or Tl; D is Fe, Ce, Cr, Sn, Zn, Pd, or Rh; E is an organic acid or a N-containing compound; a is 5–12; b is 0.01–5; c is 0.01–3; d is 0.01–3; e is 0–0.3; f is 0–10; and g is a number satisfying the valence requirements of a, b, c, d, e, and f.

The heteropolyacid catalyst of the formula 1 may have a composition of $PMo_{12}V_{0.3\sim 2}Cs_{1\sim 2}Cu_{0.1\sim 0.5}Fe_{0.01\sim 0.1}O_x$ where x is a number satisfying the valence requirements.

According to another aspect of the present invention, there is provided a method for producing the heteropolyacid catalyst represented by the formula 1, the method including:

(a) mixing $(NN_4)_6Mo_7O_{24}$, $(NH_4)VO_4$, and $H_3PO_4$, and pyridine in some cases, to prepare an aqueous solution;

(b) adding nitric acid to the solution of step (a) to prepare an ammonium ion-containing heteropolyacid;

(c) adding a transition metal carbonate to a solution obtained in step (b); and (d) drying and calcining a catalyst-containing solution obtained in step (c) in an air atmosphere.

In step (c), a transition metal nitrate may be further added.

In step (c), the transition metal carbonate and/or nitrate may be added at a temperature of 20–60° C.

Particles formed on a surface of the heteropolyacid catalyst may have a particle size of 20–100 nm.

Hereinafter, the present invention will be described in detail.

Methacrylic acid which is a product of the oxidation of methacrolein by a heteropolyacid catalyst according to the present invention is used as a monomer of polymethylmethacrylate.

The composition of the heteropolyacid catalyst of the formula 1 is based on phosphomolybdate represented by the formula, $H_3PMo_{12}O_{40}$. Phosphomolybdate has a Keggin structure in which one phosphate is surrounded by 12 octahedral molybdenum (Mo) oxides sharing edges.

The molybdenum (Mo) may be partially or wholly substituted by oxide of the A element. That is, catalyst activity can be modified by an electron effect while maintaining the same catalyst structure as phosphomolybdate. The number of cations to be bonded is determined by the oxidation state or amount of an element to be substituted. For example, when a $Mo^{+6}$ ion is substituted by a $V^{+5}$ ion, the number of cations to be bonded is increased from 3 to 4. The hydrogen ions can be substituted by alkaline metals, alkaline earth metals, transition metals, ammonium ions, or pyridine ions. The elements B, C, and D of the formula 1 represent substituted cations.

The substituted cations create a secondary or tertiary structure of a catalyst. Therefore, catalyst physical properties such as surface area, pore volume, and pore distribution can be adjusted, thereby increasing catalyst performance.

Generally, a catalyst is dried at a temperature of 100–150° C.

A dried catalyst is extruded on an extruder to prepare a catalyst with a predetermined shape. Extrusion is a very important process determining the physical strength of a catalyst. In this respect, an appropriate amount of water, a glass fiber for reinforcement of catalyst strength, etc. may be used for extrusion. An extruded catalyst has a cylindrical shape with a diameter of about 5 mm and a length of about 5 mm. The cylindrical catalyst is calcined in a furnace at 350–500° C. in an air or nitrogen atmosphere for a predetermined time. During the calcination, nitrogen oxide contained in a catalyst precursor, such as ammonia and nitrate, is removed. Also, pyridine is partially removed and combined water is gradually removed.

In the heteropolyacid catalyst of the formula 1, the most representative B element is a transition metal Cs, the most representative C element is a metal Cu, and the most representative D element is a metal Fe. Cs and Cu are derived from carbonate precursors which are commercially available. Fe is derived from a nitrate precursor and the nitrate precursor is used in a small amount in catalyst production.

The present inventors found that a catalyst with hexahedral crystal faces obtained by reaction of a previously prepared ammonium ion-containing heteropolyacid with a carbonate precursor is the most efficient catalyst. In this respect, when an ammonium ion-containing heteropolyacid is prepared and then reaction of the ammonium ion-containing heteropolyacid with a carbonate precursor is performed, a high efficiency catalyst can be produced.

A method for producing a heteropolyacid catalyst according to an embodiment of the present invention will now be described schematically.

Step (a)

$(NH_4)_6Mo_7O_{24}$, $(NH_4)VO_4$, and $H_3PO_4$, and pyridine in some cases are mixed to prepare an aqueous solution. That is, ammonium paramolybdate $((NH_4)_6Mo_7O_{24})$ and ammonium metavanadate $((NH_4)VO_4)$ are dissolved in distilled water and $H_3PO_4$ is added thereto with stirring. Pyridine is selectively added to the resultant solution and stirred to prepare an aqueous solution.

Step (b)

Nitric acid is added to the resultant solution of step (a) to prepare an ammonium ion-containing heteropolyacid. That is, $HNO_3$ is gradually dropwise added to the resultant solution of step (a) to make slurry. The slurry is stirred to prepare the ammonium ion-containing heteropolyacid.

Step (c)

Transition metal carbonate and/or nitrate is/are added to the ammonium ion-containing heteropolyacid obtained in step (b). That is, $Cu(OH)_2 \cdot CuCO_3$, $Cs_2CO_3$, and optionally $Fe(NO_3)_3$ are added to the ammonium ion-containing heteropolyacid obtained in step (b) at 20–60° C. and heated to 70° C. to increase catalyst dispersibility and activity.

Step (d)

A catalyst-containing solution obtained in step (c) is dried and calcined in an air atmosphere. That is, the catalyst-containing solution obtained in step (c) is subjected to removal of excess water in a rotary evaporator and dried in an oven. Then, the resultant product is mixed with a glass fiber and formed into a pellet of 5 mm (diameter)×5 mm (length), followed by calcination, to produce a catalyst with a particle size of 150–250 μm.

Preferably, the transition metal carbonate and/or nitrate is/are added at a temperature of 20–60° C. If the addition temperature of the transition metal carbonate and/or nitrate is less than 20° C., separate cooling is required and a production cost increases. On the other hand, if it exceeds 60° C., decomposition of carbonate may occur.

Hereinafter, the present invention will be described more specifically by Examples. However, the following Examples are provided only for illustrations and thus the present invention is not limited to or by them.

BRIEF DESCRIPTION OF THE DRAWINGS

FIG. 1 is a surface Scanning Electron Microscopy (SEM) image of a catalyst prepared in Example 2 according to the present invention.

FIG. 2 is a surface SEM image of a catalyst prepared in Example 3 according to the present invention.

FIG. 3 is a surface SEM image of a catalyst prepared in Comparative Example 1.

FIG. 4 is a surface SEM image of a catalyst prepared in Comparative Example 2.

MODES FOR CARRYING OUT THE INVENTION

EXAMPLE 1

Figure 5:
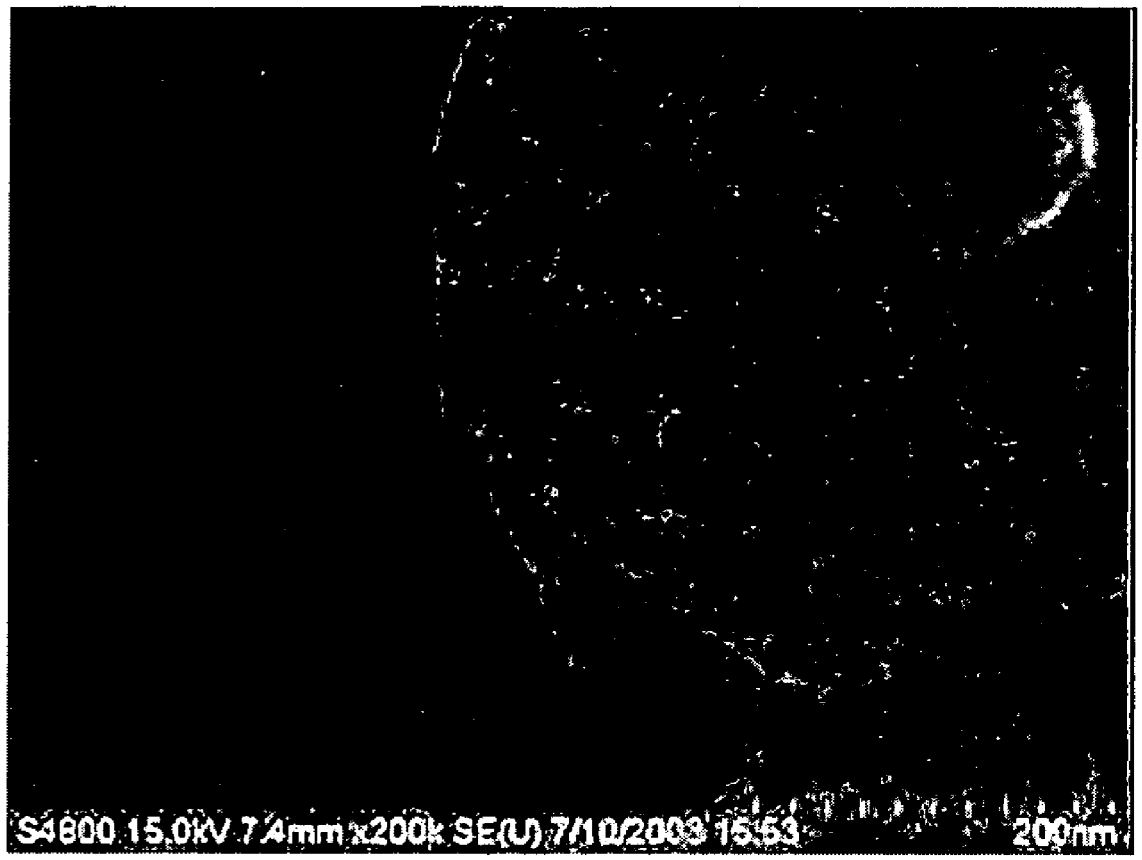
FIG. 5 is a surface SEM image of a common catalyst of Comparative Example 3.

100 g of ammonium paramolybdate $((NH_4)_6Mo_7O_{24})$ and 3.0 g of ammonium metavanadate $((NH_4)VO_4)$ were dissolved in 440 ml of 80° C. distilled water. 23 g of pyridine and 6.4 g of 85% $H_3PO_4$ were added thereto with stirring.

A solution of 60 ml of $HNO_3$ in 100 ml of $H_2O$ was gradually dropwise added to the resultant solution to make slurry. 1.7 g of $Cu(OH)_2.CuCO_3$ and 12.55 g of $Cs_2CO_3$ were added to the slurry at 40° C. with stirring and incubated at 70° C. Then, the resultant solution was subjected to removal of excess water in a rotary evaporator and dried in a 120° C. oven. The dried product was mixed with 5 g of a glass fiber, formed into pellets of 5 mm (diameter)×5 mm (length), calcined at 400° C. for 5 hours, and pulverized, to produce a catalyst with a particle size of 150–250 μm.

EXAMPLE 2

A catalyst was prepared in the same manner as in Example 1 except that 1.04 g of $Fe(NO_3)_3$ was further added, in addition to 1.7 g (7.7 mmol) of $Cu(OH)_2.CuCO_3$ and 12.55 g (38.5 mmol) $Cs_2CO_3$.

The prepared catalyst had the composition of $PMo_{12}V_{0.3\sim2}CS_{1\sim2}CU_{0.1\sim0.5}Fe_{0.01\sim0.1}O_x$ (x is a number satisfying the valence requirements) and a surface Scanning Electron Microscopy (SEM) image of the catalyst is shown in FIG. 1. The SEM image shows that 11 scale bars are written in 200 nm, and thus, a distance between the bars is 20 nm. This is also applied to Figures illustrated in the following Examples and Comparative Examples.

EXAMPLE 3

A catalyst was prepared in the same manner as in Example 2 except that pyridine was not used. A surface SEM image of the catalyst is shown in FIG. 2.

COMPARATIVE EXAMPLE 1

A catalyst was prepared in the same manner as in Example 1 except that 3.6 g (15.4 mmol) of $Cu(NO_3)_2$ and 15.0 g (77 mmol) of $CsNO_3$ were used instead of 1.7 g (7.7 mmol) of $Cu(OH)_2.CuCO_3$ and 12.55 g (38.5 mmol) of $Cs_2CO_3$. A surface SEM image of the catalyst is shown in FIG. 3.

COMPARATIVE EXAMPLE 2

A catalyst was prepared in the same manner as in Comparative Example 1 except that the transition metal precursors and nitric acid underwent coprecipitation like U.S. Pat. No. 6,458,740B2. A surface SEM image of the catalyst is shown in FIG. 4.

COMPARATIVE EXAMPLE 3

A commercially available catalyst was evaluated for catalyst performance and a surface SEM image of the catalyst is shown in FIG. 5.

Catalytic reaction results for the catalysts of Examples 1–3 and Comparative Examples 1–3 are presented in Table 1 below.

For catalyst activity evaluation, catalysts with a particle size of 150–250 μm obtained by pulverization of calcined pellets were used to minimize the effect of the pressure change.

Catalytic reaction was performed under the composition of 3.6 mol % of methacrolein (MACR), 10 mol % of $H_2O$, 9.2 mol % of $O_2$, and balance $N_2$. A dose of a used catalyst was 1 g. The reaction temperature was 280–320° C. A product was quantified by Gas Chromatography (GC).

Methacrolein conversion rate, and methacrylic acid yield and selectivity were respectively calculated by Equations 1–3 below:

Methacrolein conversion rate (%)=[moles of reacted methacrolein/moles of supplied methacrolein]× 100     [Equation 1]

Selectivity (%)=[moles of produced methacrylic acid/moles of reacted methacrolein]×100     [Equation 2]

Yield (%)=[moles of produced methacrylic acid/moles of supplied methacrolein]×100=conversion rate×selectivity     [Equation 3]

TABLE 1

| Example | Reaction temperature (° C.) | Conversion rate (%) | Selectivity (%) | Yield (%) |
| --- | --- | --- | --- | --- |
| Example 1 | 280 | 34.01 | 80.30 | 27.31 |
|  | 300 | 45.24 | 81.54 | 36.89 |
| Example 2 | 280 | 36.19 | 80.16 | 29.01 |
|  | 300 | 49.58 | 80.99 | 40.16 |
| Example 3 | 280 | 34.32 | 73.67 | 25.28 |
| Comparative Example 1 | 280 | 21.07 | 66.71 | 14.06 |
|  | 300 | 31.98 | 74.17 | 23.72 |
| Comparative Example 2 | 280 | 15.49 | 51.41 | 8.45 |
|  | 300 | 28.34 | 67.29 | 19.07 |
| Comparative Example 3 | 280 | 30.13 | 76.19 | 22.95 |

As cane be seen from Table 1, the catalysts prepared in Examples 1–3 according to the present invention exhibited remarkably excellent conversion rate, selectivity, and yield, as compared with the catalysts of Comparative Examples 1–3 according to conventional technologies. In connection with the catalysts shown in FIGS. 1 and 2 according to the present invention, particles of 20 to 100 nm in size were uniformly distributed on surfaces of the catalysts, relative to the catalysts of Comparative Examples 1–3. This shows that transition metal ions were uniformly dispersed.

Industrial Applicability

As apparent from the above description, a heteropolyacid catalyst of the present invention is excellent in conversion rate, selectivity, and yield, relative to that produced by a conventional heteropolyacid catalyst production technology.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heteropolyacid catalyst represented by the following formula 1:

wherein A is V, Nb, or W; B is an alkali metal or an alkaline earth metal; C is a transition metal selected from the group consisting of Cu, Ag, Co, Ni, and Mn; D is Fe, Ce, Cr, Sn, Zn, Pd, or Rh; E is an organic acid or a N-containing compound; a is 5–12; b is 0.01–5; c is 0.01–3; d is 0.01–3; e is 0–0.3; f is 0–10; and g is a number satisfying the valence requirements of a, b, c, d, e, and f; and wherein transition metal ions are uniformly dispersed.

2. The heteropolyacid catalyst of claim 1, which has a composition of $PMo_{12}V_{0.3\sim2}Cs_{1\sim2}Cu_{0.1\sim0.5}Fe_{0.01\sim0.1}O_x$ where x is a number satisfying the valence requirements.

3. A method for producing the heteropolyacid catalyst of claim 1, the method comprising:

(a) mixing $(NH_4)_6Mo_7O_{24}$, $(NH_4)VO_4$, and $H_3PO_4$, and optionally pyridine, to prepare an aqueous solution;

(b) adding nitric acid to the solution of step (a) to prepare an ammonium ion-containing heteropolyacid;

(c) adding a transition metal carbonate and an alkali or alkaline earth metal carbonate to a solution obtained in step (b); and (d) drying and calcining a catalyst-containing solution obtained in step (c) in an air atmosphere.

4. The method of claim 3, wherein in step (c), a transition metal nitrate is further added.

5. The method of claim 4, wherein in step (c), the transition metal carbonate and nitrate are added at a temperature of 20–60° C.

6. The method of claim 3, wherein in step (c), the transition metal carbonate is added at a temperature of 20–60° C.

7. The method of claim 3, wherein particles formed on a surface of the heteropolyacid catalyst have a particle size of 20–100 nm.

* * * * *